US006303111B1

(12) United States Patent
Maurer et al.

(10) Patent No.: US 6,303,111 B1
(45) Date of Patent: Oct. 16, 2001

(54) NONTOXIC BIOCOMPATIBLE DEODORIZING COMPOSITIONS

(75) Inventors: Gerald L. Maurer, Cincinnati, OH (US); David Melzer, Chicago, IL (US)

(73) Assignee: National Research Labs, Cincinnati, OH (US)

( * ) Notice: Subject to any disclaimer, the term of this patent is extended or adjusted under 35 U.S.C. 154(b) by 0 days.

(21) Appl. No.: 09/328,101

(22) Filed: Jun. 8, 1999

(51) Int. Cl.[7] ................................. A61L 9/01; A61L 9/04
(52) U.S. Cl. ............... 424/76.1; 424/76.2; 424/76.21; 424/76.4; 424/76.6; 424/76.8
(58) Field of Search .................... 424/76.1, 76.2, 424/76.21, 76.22, 76.4, 76.6, 76.8

(56) References Cited

U.S. PATENT DOCUMENTS

| | | | |
|---|---|---|---|
| 4,055,655 | 10/1977 | Maurer et al. | 424/294 |
| 4,385,632 | 5/1983 | Odelhög | 604/360 |
| 4,666,616 | 5/1987 | Rossmoore | 252/11 |
| 4,680,309 | 7/1987 | Maurer | 514/499 |
| 4,707,282 | 11/1987 | Rossmoore | 255/11 |
| 4,708,808 | 11/1987 | Rossmoore | 252/11 |
| 5,047,022 | 9/1991 | Hasebe et al. | 604/359 |
| 5,076,960 | 12/1991 | Hutchings et al. | 252/186.33 |
| 5,534,249 | 7/1996 | Maurer | 424/76.3 |
| 5,813,058 | 9/1998 | Quigley et al. | 4/309 |

*Primary Examiner*—Shelley A. Dodson
(74) *Attorney, Agent, or Firm*—Dinsmore & Shohl LLP

(57) ABSTRACT

Nontoxic biocompatible deodorizing compositions are essentially free of nonbiocompatible components and comprise, by volume, from about 0.05 to about 0.5 percent of an odor elimination agent, in combination with a physiologically compatible buffering agent, a wetting agent and a polar diluent. The compositions are suitable dispensed from a spray dispenser and are adapted for reducing malodors in environments where contact of the compositions with humans or animals having compromised or reduced chemical or microbiological resistance is anticipated or not easily prevented, for example in operating rooms, intensive care units, neonatal nurseries, and additional health care facilities.

28 Claims, No Drawings

NONTOXIC BIOCOMPATIBLE DEODORIZING COMPOSITIONS

FIELD OF THE INVENTION

The present invention is directed to biocompatible deodorizing compositions, and more particularly to such compositions which eliminate malodors by chemical reaction with odorogenic molecules rather than by masking malodors. The compositions are free of toxic components and therefore are advantageous for use in environments where contact of the compositions with humans having compromised or reduced chemical or microbiological resistance is anticipated or not easily prevented, for example in health care facilities and the like.

BACKGROUND OF THE INVENTION

Numerous deodorizing compositions are known in the art and are commercially available. Many such compositions include perfumes and the like for masking malodors. Compositions which rely on perfumes for masking malodors typically have limited effectiveness in deodorizing properties and are generally ineffective once the perfume component has dispersed. On the other hand, compositions which employ odor elimination agents which react with odor causing materials are typically more effective in reducing malodors. For example, the Maurer U.S. Pat. No. 5,534,249 discloses methods for reducing malodors by use of complexes of metals and polyfunctional organic ligands which neutralize, rather than merely mask, odor causing materials. Maurer discloses compositions containing about 5 weight percent of disodium monocopper citrate for use in ammonia-containing cold room environments and carpet deodorizinl) compositions containing about 20 weight percent monozinc citrate.

Although it is often desirable to employ deodorizing compositions in health care facilities to eliminate malodors, it is frequently not safe to do so in environments where compromised resistance to chemical and/or microbiological challengies are common, for example in operating rooms, intensive care units, neonatal nurseries and the like. That is, compositions adapted for spraying as a mist or aerosol in such environments will typically come into contact, or at least are not easily prevented from coming into contact, with the skin, eyes and/or mucous membranes of the oro-nasal and/or respiratory tracts of those in the proximate area of application. Absorption into the blood can result from such contact, for example through the mucous membranes, amounting to parenteral administration of the components from such sprays, and such contact can often be detrimental to an individual's health, particularly in humans or animals having compromised resistance. As many conventional deodorizing compositions contain components which will exhibit one or more disadvantageous effects upon this type of human contact, it is not safe to spray such deodorizing compositions in these environments.

For example, various conventional deodorizing spray ingredients include cocoamidopropyl betaine (a contact dermatitis agent), formaldehyde (a protein denaturant, skin sensitizer and probable carcinogen), morpholinium (an eye irritant and skin sensitizer), adamantane (a neurotransinission contact blocker, systemic sensitizer and possible reactant with RNA), benzalkonium chloride (a skin sensitizer), ethanol and/or methanol (teratogenic/neurotoxic agents), triethylene glycol (a neuromuscular depressor), and quaternary ammonium compounds (skin sensitizers), and the like. Thus, deodorizing compositions containing such components are not safe for use in environments where contact of the compositions with humans having compromised resistance to chemical or microbiological challenges is anticipated or not easily prevented, for example in health care facilities such as operating rooms, intensive care units, neonatal nurseries and the like, and a need exists for deodorizing compositions which can be safely employed in such environments.

SUMMARY OF THE INVENTION

Accordingly, it is an object of the present invention to provide improved deodorizing compositions. It is an additional object of the present invention to provide biocompatible deodorizing compositions which overcome disadvantages of the prior art. It is a more specific object of the invention to provide biocompatible deodorizing compositions which neutralize, rather than merely mask, odor causing materials. It is a further object of the invention to provide such compositions which are safe for use in environments where contact of the compositions with humans having compromised chemical and/or microbiological resistance is anticipated or not easily prevented, for example in health care facilities such as operating rooms, intensive care units, neonatal nurseries and the like.

These and additional objects are provided by the biocompatible deodorizing compositions of the present invention. More particularly, the invention is directed to nontoxic biocompatible deodorizing compositions which are essentially free of nonbiocompatible components. The compositions comprise, by volume, from about 0.05 to about 0.5 percent of an odor elimination agent, in combination with a physiologically compatible buffering agent, a wetting agent and a polar diluent. That the compositions are essentially free of nonbiocompatible components means that the compositions do not contain a functional amount of any substance which, upon contact with normal human or animal tissue, causes a detectable alteration of the normal structure or function of the tissue. A functional amount as used herein means an amount sufficient to cause a detectable alteration of the normal structure or function of the tissue upon contact with normal human or animal tissue. Preferably, the compositions are entirely free of any such substance which, upon contact with normal human or animal tissue, causes a detectable alteration of the normal structure or function of the tissue.

The invention is further directed to articles of manufacture which comprise a biocompatible deodorizing composition packaged in a container having a spray dispenser. The biocompatible deodorizing composition comprises, by volume, from about 0.05 to about 0.5 percent of an odor elimination agent, in combination with a physiologically compatible buffering agent, a wetting agent and a polar diluent, the composition being essentially free of nonbiocompatible components. In an additional embodiment, the invention is directed to methods of reducing malodors in an environment where contact of the compositions with humans or animals having compromised or reduced resistance to chemical and/or microbiological challenges is anticipated or not easily prevented. The methods comprise spraying a biocompatible deodorizing composition in the environment, the biocompatible deodorizing composition comprising, by volume, from about 0.05 to about 0.5 percent of an odor elimination agent, in combination with a physiologically compatible buffering agent, a wetting agent and a polar diluent, the composition being essentially free of nonbiocompatible components.

The compositions, articles of manufacture and methods according to the present invention are advantageous in that they are effective in safely reducing and/or eliminating malodors, particularly in environments where contact of the compositions with humans having compromised and/or reduced resistance is anticipated or not easily prevented, for example in health care facilities such as operating rooms, intensive care units, neonatal nurseries and the like.

These and additional objects and advantages provided by the compositions, articles of manufacture and methods of the present invention will be more fully apparent in view of the following detailed description.

DETAILED DESCRIPTION

The biocompatible deodorizing compositions according to the present invention comprise, by volume, from about 0.05 to about 0.5 percent of an odor elimination agent, in combination with a physiologically compatible buffering agent, a wetting agent and a polar diluent, the composition being essentially free of nonbiocompatible components. That the compositions are essentially free of nonbiocompatible components means that the compositions do not contain a functional amount, and preferably do not contain any measurable amount, of any substance which, upon contact with normal human or animal tissue, causes a detectable alteration of the normal structure or function of the tissue. A functional amount as used herein means an amount sufficient to cause a detectable alteration of the normal structure or function of the tissue upon contact with normal human or animal tissue.

The odor elimination agent may be any suitable agent which reacts with odorogenic molecules to reduce malodors, rather than merely masking odor causing materials. In a preferred embodiment, the odor elimination agent comprises a complex of one or more metals and a polyfunctional ligand. In a further preferred embodiment, the odor elimination agent comprises a complex of one or more metals and a polyfunctional organic ligand. Suitable metal complexes include, but are not limited to, those disclosed in the Maurer et al U.S. Pat. Nos. 4,055,655 and 4,278,610, both of which are incorporated herein by reference. Typically, the metal ion which forms the complex may comprise a monovalent or polyvalent ion. Divalent metals such as copper and zinc are preferred. The polyfunctional ligand may be organic or inorganic in nature, with such ligands being known in the art. Preferred polyfunctional organic ligands comprise an alpha or beta hydroxy carboxylic acid, for example citric acid, or, alternatively, another functionally substituted acid such as an alpha or beta amino, sulfhydro, phosphinol or the like substituted carboxylic. A preferred polyfunctional organic ligand comprises citric acid. In an additionally preferred embodiment, the complex comprises a 1:1 mono-metal:polyfunctional organic ligand chelate, or a salt thereof. Monoalkali and polyalkali salts are preferred. Examples of specific complexes for use in the present invention include disodium monocopper citrate and disodium monozinc citrate. Extensive toxicological testing of these complexes indicates they are biocompatible and safe for the embodiments disclosed herein.

The physiologically compatible buffering agent employed in the present compositions may comprise any of the known buffering agents which are physiologically compatible in the amounts employed. Physiologically compatible buffers known in the art include, but are not limited to, citric acids or salts thereof, sodium phosphate, sodium biphosphate, sodium carbonate, sodium bicarbonate, or mixtures thereof. Conventional borate buffers are specifically excluded as such buffers can exhibit toxic or otherwise adverse effects on humans and/or animals. The buffering agent may be employed to adjust the pH of the deodorizing compositions to a neutral value of around 7.0–8.0. Preferably, the pH of the compositions is in the range of from about 7.0 to about 7.5, and more preferably in the range of from about 7.1 to about 7.2.

The wetting agent which is employed in the biocompatible deodorizing compositions according to the present invention may comprise any physiologically compatible wetting agent which facilitates spray dispensing of the compositions. The wetting agent reduces the particle size of the composition in spray form and surprisingly improves the efficacy of the compositions, thereby allowing a small amount of sprayed composition, for example 0.01 to 10 ml, more preferably from about 0.1 to about 1 ml, to effectively eliminate malodors in a surrounding environment. In a preferred embodiment, the wetting agent comprises a fatty acid ethoxylate. The fatty acid moiety may comprise from about 4 to about 22 carbons and preferably comprises from about 12 to about 20 carbon atoms, and is ethoxylated with from about 2 to about 30 ethloxy groups, more preferably from about 2 to about 20 ethoxy groups, per molecule. Suitable fatty acid ethoxylates are available commercially under the tradename Tween.

The fourth essential component of the biocompatible deodorizing compositions of the present invention comprises the polar diluent. Preferably, the polar diluent is purified water. Diluents which have a teratogenic and/or neurotoxic effect on humans having compromised chemical and/or microbiological resistance, for example ethanol and methanol which are commonly employed in conventional compositions, are specifically excluded from the compositions of the present invention. The water can be purified by any suitable means including deionization, reverse osmosis techniques, ultraviolet radiation or the like.

Surprisingly, the biocompatible deodorizing compositions are effective for reducing malodors while containing a relatively small amount of the odor elimination agent, for example in the range of from about 0.05 to about 0.5 volume percent. More preferably, the compositions comprise from about 0.05% to about 0.2% by volume of the odor elimination agent. In further preferred embodiments, the biocompatible deodorizing compositions comprise, by volume percent, from about 0.05% to about 0.5% of the odor elimination agent, from about 0.01% to about 0.5% of the physiologically compatible buffering agent, from about 0.1% to about 1% of the wetting agent, and from about 98% to about 99.5% of water. In a further preferred embodiment, the compositions comprise, by volume percent, from about 0. 1% to about 0.3% of the odor elimination agent, from about 0.05% to about 0.25% of the physiologically compatible buffering agent, from about 0.25% to about 0.75% of the wetting agent, and from about 98.5% to about 99.5% water. As discussed above, the compositions are essentially free of nonbiocompatible components, and more preferably the compositions are entirely free of nonbiocompatible components. It has surprisingly been determined that such low concentrations of the indicated combination of components provide unexpectedly high efficacy for reducing malodors, even when sprayed in relatively small amounts as discussed above. Simultaneously, the compositions may be used in environments where contact with humans having compromised and/or reduced resistance to chemical and/or microbiological components is anticipated or not easily prevented as contact of the compositions with such humans does not cause adverse effects.

The compositions may optionally include one or more additional biocompatible components as desired. For example, depending on the desired mode of dispensing the compositions, it may be suitable to include a preservative in the compositions. Biocompatible preservatives must be non-toxic and chemically compatible with the odor elimination agent and the additional components of the compositions while preventing bacterial growth therein. Examples of such preservatives include, but are not limited to, the parabens and Bronopol (2-bromo-2-nitropropane-1,3-diol). Suitably, the preservative, if included, is employed in effective amount less than about 0.1 volume percent, more preferably less than about 0.05 volume percent.

The compositions may further optionally include a perfume component to provide a pleasant scent. It is important to recognize, however, that the perfume component is not employed to mask malodors as the odor elimination agent reacts with odorogenic molecules to neutralize the malodors.

The compositions are particularly adapted for packaging in a container having a spray dispenser. Preferably, the components of the compositions are mixed and passed through a suitable sterilizing filter system, for example a commercially available Pall Filtration sterile filtration system, to provide a product that is free from potentially harmful microorganisms and obviate transmission of infectious disease. The composition may be packaged in an aerosol container provided with a self-pressurized aerosol spray dispensing system. An aerosol container requires no displacement of air from the environment, whereby the sterility of the composition packaged therein may be maintained even upon spraying of the composition from the container. Any propellant known in the art may be used in such aerosol containers. Preferably, the propellant will comprise carbon dioxide or nitrogen as these propellants more efficiently provide for smaller particle size spray droplets. Suitable pressures range from about 50 to about 60 psi, although other pressures may be employed.

Alternatively, the filtered composition may be packaged in a container having a pump-type spray dispenser, various embodiments of which are well known in the packaging art. As the dispensed composition is replaced by ambient air in a pump-type spray dispenser, the compositions which are packaged in a container having a pump-type spray dispenser should include a biocompatible preservative as described above to prevent bacterial growth in the composition. In another alternate embodiment, the compositions may be employed in an electrical spray dispenser, for example in operating rooms, intensive care units and other health care facilities. Additional spray dispensers known in the art may also be used in combination with a container in which the biocompatible deodorizing compositions of this invention are packaged.

The compositions, articles of manufacture and methods according to the present invention are illustrated by the following example which is intended to be nonlimiting of the invention disclosed herein.

EXAMPLE

A composition according to the present invention is prepared by combining the following components:

| Component | Volume Percent |
|---|---|
| Purified water | 99.14% |
| Fatty acid ethoxylate wetting agent (Tween 80) | 0.53% |

-continued

| Component | Volume Percent |
|---|---|
| Monocopper citrate odor elimination agent | 0.20% |
| Sodium citrate buffering agent | 0.10% |
| Bronopol preservative | 0.03% |

The mixture is passed through a sterilizing filter system and packaged in a container having a pump-type spray dispenser. The composition is sprayed in operating rooms, intensive care units and/or neonatal nurseries to reduce malodors therein, without causing any adverse effects upon human contact therein.

The present example and the specific embodiments set forth in the present specification are provided to illustrate various embodiments of the invention and are not intended to be limiting thereof. Additional embodiments within the scope of the present claims will be apparent to one of ordinary skill in the art.

What is claimed is:

1. A biocompatible deodorizing composition, the composition being essentially free of nonbiocompatible components and comprising, by volume, from about 0.05 to about 0.5 percent of an odor elimination agent, in combination with a physiologically compatible buffering agent, a wetting agent and a polar diluent.

2. A biocompatible deodorizing composition as defined by claim 1, comprising from about 0.05 to about 0.2 percent of the odor elimination agent.

3. A biocompatible deodorizing composition as defined by claim 2, wherein the odor elimination agent comprises a complex of at least one metal and a polyfunctional ligand.

4. A biocompatible deodorizing composition as defined by claim 3, wherein the odor elimination agent comprises a complex of at least one metal and a polyfunctional organic ligand.

5. A biocompatible deodorizing composition as defined by claim 3, wherein the odor elimination agent comprises a monometal citrate.

6. A biocompatible deodorizing composition as defined by claim 3, wherein the odor elimination agent comprises monocopper citrate or monozinc citrate.

7. A biocompatible deodorizing composition as defined by claim 1, wherein the physiologically compatible buffering agent comprises citric acid or a salt thereof, sodium phosphate, sodium biphosphate, sodium carbonate, sodium bicarbonate, or mixtures thereof.

8. A biocompatible deodorizing composition as defined by claim 1, wherein the composition has a pH of from about 7 to about 7.5.

9. A biocompatible deodorizing composition as defined by claim 1, wherein the wetting agent comprises a fatty acid ethoxylate.

10. A biocompatible deodorizing composition as defined by claim 1, wherein the polar diluent comprises purified water.

11. A biocompatible deodorizing composition, comprising, by volume, from about 0.05 to about 0.5 percent of an odor elimination agent, from about 0.01 to about 0.5 percent of a physiologically compatible buffering agent, from about 0.1 to about 1 percent of a wetting agent, and from about 98 to about 99.5 percent water.

12. A biocompatible deodorizing composition as defined by claim 11, comprising, by volume, from about 0.1 to about 0.3 percent of the odor elimination agent, from about 0.05 to about 0.25 percent of the physiologically compatible buffering agent, from about 0.25 to about 0.75 percent of the wetting agent, and from about 98.5 to about 99.5 percent water.

13. A biocompatible deodorizing composition as defined by claim 1, wherein the composition has been filtered through a sterilizing filter.

14. A biocompatible deodorizing composition as defined by claim 1, further comprising a biocompatible preservative.

15. An article of manufacture, comprising a biocompatible deodorizing composition packaged in a container having a spray dispenser, the biocompatible deodorizing composition being essentially free of nonbiocompatible components and comprising, by volume, from about 0.05 to about 0.5 percent of an odor elimination agent, in combination with a physiologically compatible buffering agent, a wetting agent and a polar diluent.

16. An article of manufacture as defined by claim 15, wherein the container comprises a self pressurized aerosol spray container.

17. An article of manufacture as defined by claim 15, wherein the container comprises a pump spray container.

18. An article of manufacture as defined by claim 17, wherein the composition further comprises a biocompatible preservative.

19. An article of manufacture as defined by claim 15, wherein the odor elimination agent comprises a complex of at least one metal and a polyfunctional ligand.

20. An article of manufacture as defined by claim 15, wherein the odor elimination agent comprises a complex of at least one metal and a polyfunctional organic ligand.

21. A method of reducing malodors in an environment wherein contact of the composition with humans or animals having reduced chemical or microbiological resistance is anticipated, comprising spraying a biocompatible deodorizing composition in a malodorous area of the environment, the biocompatible deodorizing composition being essentially free of nonbiocompatible components and comprising, by volume, from about 0.05 to about 0.5 percent of an odor elimination agent, in combination with a physiologically compatible buffering agent, a wetting agent and a polar diluent.

22. A method as defined by claim 21, wherein the biocompatible deodorizing composition comprises, by volume, from about 0.1 to about 0.3 percent of the odor elimination agent, from about 0.05 to about 0.25 percent of the physiologically compatible buffering agent, from about 0.25 to about 0.75 percent of the wetting agent, and from about 98.5 to about 99.5 percent water.

23. A method as defined by claim 21, wherein the odor elimination agent comprises a complex of at least one metal and a polyfunctional ligand.

24. A method as defined by claim 21, wherein the odor elimination agent comprises a complex of at least one metal and a polyfunctional organic ligand.

25. A method as defined by claim 21, wherein the odor elimination agent comprises monocopper citrate or monozinc citrate.

26. An article of manufacture as defined by claim 15, wherein the biocompatible deodorizing composition comprises, by volume, from about 0.1 to about 0.3 percent of the odor elimination agent, from about 0.05 to about 0.25 percent of the physiologically compatible buffering agent, from about 0.25 to about 0.75 percent of the wetting agent, and from about 98.5 to about 99.5 percent water.

27. An article of manufacture as defined by claim 26, wherein the biocompatible deodorizing composition has a pH of from about 7 to about 7.5.

28. A biocompatible deodorizing composition as defined by claim 11, wherein the composition has a pH of from about 7 to about 7.5.

* * * * *